(12) United States Patent
Zoppi et al.

(10) Patent No.: US 12,064,492 B2
(45) Date of Patent: Aug. 20, 2024

(54) CELLS LOADED WITH GOLD NANOPARTICLES FOR USE IN THE DIAGNOSIS AND/OR TREATMENT OF MELANOMA

(71) Applicants: Consiglio Nazionale delle Ricerche, Rome (IT); Plasma Diagnostics and Technologies S.r.l., Pisa (IT); Universita degli Studi di Firenze, Florence (IT)

(72) Inventors: Angela Zoppi, Florence (IT); Mario Del Rosso, Pistoia (IT); Anna Laurenzana, Tricarico (IT); Gabriella Fibbi, Florence (IT); Francesca Margheri, Empoli (IT); Anastasia Chilla', Florence (IT); Giancarlo Margheri, Rome (IT)

(73) Assignee: Universita degli Studi di Firenze, Florence (IT)

( * ) Notice: Subject to any disclaimer, the term of this patent is extended or adjusted under 35 U.S.C. 154(b) by 0 days.

(21) Appl. No.: 16/096,505

(22) PCT Filed: May 3, 2017

(86) PCT No.: PCT/IB2017/052567
§ 371 (c)(1),
(2) Date: Oct. 25, 2018

(87) PCT Pub. No.: WO2017/191572
PCT Pub. Date: Nov. 9, 2017

(65) Prior Publication Data
US 2019/0142980 A1    May 16, 2019

(30) Foreign Application Priority Data

May 4, 2016 (IT) .................. 102016000045932

(51) Int. Cl.
*A61K 9/00* (2006.01)
*A61K 33/242* (2019.01)
(Continued)

(52) U.S. Cl.
CPC ........ *A61K 51/1203* (2013.01); *A61K 33/242* (2019.01); *A61K 35/28* (2013.01);
(Continued)

(58) Field of Classification Search
CPC .................................................. A61K 51/1203
See application file for complete search history.

(56) References Cited

U.S. PATENT DOCUMENTS

2012/0141562 A1* 6/2012 Achneck ............... A61L 27/06
424/400

FOREIGN PATENT DOCUMENTS

JP        2003305124 A    10/2003

OTHER PUBLICATIONS

Letfullin, Modeling nanophotothermal therapy: kinetics of thermal ablation of health and cancerous cell organells and gold nanoparticles, Nanomedicine: Nanotechnology, Biologiy, and Medicine, 2011, 8, 137-145. (Year: 2011).*

(Continued)

*Primary Examiner* — Paul W Dickinson
(74) *Attorney, Agent, or Firm* — LUCAS & MERCANTI, LLP

(57) ABSTRACT

The present invention refers to cells from a subpopulation of progenitors of endothelial cells loaded with gold nanoparticles sensitive to excitation with infrared radiation with consequent release of thermal energy, to a composition having a plurality of these cells and to their use in the diagnosis and treatment of solid tumours thanks to the selective localization of the composition in the tumour mass, which can be thus identified easily for diagnostic purposes (Continued)

by marking the cells with appropriate marking agents, or treated by stimulation with pulsed laser beam up to the complete cauterization of the tumour mass for a targeted and highly effective therapeutic action.

13 Claims, 6 Drawing Sheets

(51) Int. Cl.
  *A61K 35/28*   (2015.01)
  *A61K 41/00*   (2020.01)
  *A61K 47/69*   (2017.01)
  *A61K 49/00*   (2006.01)
  *A61K 51/12*   (2006.01)
  *A61P 35/00*   (2006.01)

(52) U.S. Cl.
  CPC ...... *A61K 41/0052* (2013.01); *A61K 47/6901* (2017.08); *A61K 49/0065* (2013.01); *A61P 35/00* (2018.01)

(56) References Cited

OTHER PUBLICATIONS

Baginskiy, Chitosan-Modified Stable Colloidal Gold Nanostars for the Photothermolysis of Cancer Cells, The Journal of Physical Chemistry C, 2013, 117, 2396-2410. (Year: 2013).*

Margheri, Tumor-tropic endothelial colony forming cells (ECFCs) loaded with near-infrared sensitive Au nanoparticles: A "cellular stove" approach fo the photoablation of melanoma, Ontarget, 2016, 7(26), 39846-30960. (Year: 2016).*

Wang et al., "Fluorescent gold nanoclusters as a biocompatible marker for in vitro and in vivo tracking of endothelial cells", ACS Nano, 2011, vol. 5, No. 6, pp. 4337-4344.

Kang et al., "Mesenchymal Stem Cells Aggregate and Deliver Gold Nanoparticles to Tumors for Photothermal Therapy", ACS Nano, 2015, vol. 9, No. 10, pp. 9678-9690.

Laurenzana et al., "Melanoma cell therapy: Endothelial progenitor cells as shuttle of the MMP12 uPAR-degrading enzyme", Oncotarget, 2014, vol. 5, No. 11. pp. 3711-3727.

Margheri et al., "Tumor-tropic endothelial colony forming cells (ECFCs) loaded with near-infrared sensitive Au nanoparticles: A "cellular stove" approach to the photoablation of melanoma", Oncotarget, 2016, vol. 7, No. 26, pp. 39846-39860.

International Search Report and Written Opinion for Corresponding International Application No. PCT/IB2017/052567 (10 Pages) (Aug. 29, 2017).

Baginskiy et al., "Chitosan-Modified Stable Colloidal Gold Nanostars for the Photothermolysis of Cancer Cells", J. Phys. Chem. C, 2013, vol. 117, No. 5, pp. 2396-2410.

Li et al., "Small gold nanorods laden macrophages for enhanced tumor coverage in photothermal therapy". Biomaterials, 2016, vol. 74, pp. 144-154.

Office Action for Corresponding Japanese Patent Application No. 2019-510485, Oct. 22, 2020, pp. 1-4, English translation 4 pages.

* cited by examiner

CELLS LOADED WITH GOLD NANOPARTICLES FOR USE IN THE DIAGNOSIS AND/OR TREATMENT OF MELANOMA

CROSS-REFERENCE TO RELATED APPLICATIONS

This application is a 371 of PCT/IB2017/052567, filed May 3, 2017, which claims the benefit of Italian Patent Application No. 102016000045932, filed May 4, 2016.

FIELD OF THE INVENTION

The present invention relates in general to the pharmaceutical field, and more precisely it refers to a subpopulation of progenitors of endothelial cells marked with a marking agent and loaded with gold nanoparticles, and to their use in the diagnosis and treatment of melanoma and of its possible metastasis, and of other solid tumours.

STATE OF THE ART

One of the most important challenges to overcome in oncology is currently the identification of specific tumour molecular targets, since the phenotype of cancer cells is often similar to that of normal cells (often the existing differences are more quantitative rather than qualitative) and there is a large variability of alterations among different types of tumour.

Recent scientific advances in the field of cellular and molecular biotechnology have opened new advanced therapeutic boundaries such as somatic cell gene therapy and nanomedicine, for the treatment of various diseases, for which there are not always effective treatments, and in particular for tumours. One of the most aggressive forms of malignant tumour is melanoma, whose incidence is continually increasing: an increase in incidence of 3-7% per year was observed in recent years as well as an increase in mortality of approximately 2% per year.

The increase in incidence is closely related to the increased early diagnosis of "thin" forms of melanoma (thickness<1 mm, with good prognosis), while the increase in mortality appears to be mainly due to the lack of reduction of the "thick" forms (thickness>1 mm, with bad prognosis). While early-diagnosed melanoma can be efficiently treated with surgical excision, advanced stages are known to be refractory to conventional therapies. It is therefore essential to find "alternative therapies" in order to obtain the inhibition of tumour growth and of neoplastic progression of melanoma, thus directing the patient to the most appropriate therapy.

Amongst the alternative therapies is in great expansion the so-called "nanomedicine" based on the use as therapeutic agents of metallic nanoparticles, in particular of gold nanoparticles, which can absorb in the near infrared spectrum and develop heat following laser beam stimulation. Thanks to these properties and the fact that they are not toxic to healthy tissues, these nanoparticles are currently one of the most interesting applications in the fight against tumours as they can induce "thermoablation" in many types of cancer when they are irradiated with light in the near infrared.

For a real use of such nanoparticles in tumour therapy, however, there are still many obstacles to overcome, mainly related to their bio-distribution in the subject in which they are injected and therefore to their recruitment within the tumour mass to be subjected to thermoablation. In this regard, it is commonly accepted in the scientific community that the metallic nanoparticles passively accumulate in the tumour mass due to the effect so-called Enhanced Permeability and Retention (EPR), attributable both to the increased permeability of tumour vessels and to the lack of an effective drainage by the lymphatic tumour system, leading to a local accumulation of the substances penetrated into the tissue. Actually, it has been shown that the nanoparticles are also distributed in the various healthy organs and tissues, and only a small percentage of inoculated "naked" nanoparticles are able to locate in the tumour (see, for example, Maeda H. et al., "The EPR Effect of macromolecular drug delivery to solid tumors: Improvement of tumor absorption, lowering of systemic toxicity and distinct tumor imaging in vivo "Adv Drug Deliv Rev. 2013; 65: 71-9), from which the various strategies derive of nanoparticles functionalization with molecules capable of conveying nanoparticles to certain tumour tissues so as to enrich their presence in such tissues with respect to the surrounding healthy tissues (Sun T. et al., "Engineered nanoparticles for drug delivery in cancer therapy", Angew Chem Int.: 12320-64).

To date, however, it cannot be said that the problem of the off-target toxicity of the metallic nanoparticles due to their distribution in tissues and healthy organs has also been solved because of the fact that such nanoparticles can be distributed in healthy tissues and organs through multiple mechanisms, such as endothelial transcytosis, or the formation of vesicle-vacuolar organelles (VVO) or, in some organs such as endocrine glands, intestines, pancreas and kidney glomeruli, the nanoparticles may be distributed in such healthy organs due to the presence of fenestrated endothelium. The sinusoidal capillaries present in the bone marrow, in lymph nodes, spleen and liver also allow the passage of substances, including nanoparticles, through the openings present at the cellular joints. Finally, the important role played by the macrophages system MPS (Mononuclear Phagocyte System), which, in physiological conditions and at various tissues and organs, is able to phagocyte the nanoparticles thus determining their accumulation in these healthy tissues and organs.

In addition to the off-target toxicity, another problem not yet overcome is that of the metallic nanoparticles clearance once their diagnostic and/or therapeutic action is completed. To make it possible to use nanoparticles in humans, it is necessary that they be completely eliminated from the body over a reasonable period of time to avoid creating accumulation of metals in the body which could in turn generate long-term toxicity and create interference with other diagnostic techniques, such as radiology.

For all the reasons set out above, despite the great expectations created in the scientific community in recent years, the metallic nanoparticles have not yet been transferred as diagnostic and/or therapeutic agents from use in animal models to actual human use. On the other hand, given the increasing incidence of certain tumour forms, such as melanoma, and given the undeniable intriguing properties shown by the nanoparticles as diagnostic and/or therapeutic agents in the oncology field, the need to find an effective strategy for the delivery of metallic nanoparticles to target tumours such as melanoma and metastases thereof, which allows reducing the risk of off-target toxicity but also the risk involved in the accumulation in the body for insufficient or slow excretion of nanoparticles.

SUMMARY OF THE INVENTION

Now the inventors have surprisingly identified a subpopulation of progenitors of endothelial cells named endothelial forming colony cells, herein below also indicated with the acronym ECFC (Endothelial Colony Forming Cells), which is an optimal carrier for gold nanoparticles having a peak of absorbance in the near infrared that are incorporated in the cells and, once injected in an organism, localize in the tumour mass of the melanoma. Furthermore, the permanence of the ECFC loaded with nanoparticles in the main organs, such as liver and kidneys, proved to be transitory.

The cells loaded with nanoparticles according to the invention allow in particular, thanks to the appropriate marking of the cells, carrying out diagnostic analyses and identifying the melanoma tumour mass by a technique suitable for detecting the marking agent in the organism; and at the same time, once localized in the tumour mass, they allow cauterizing the tumour by thermoablation, with an approach definable as a whole as "theranostic", i.e. having a double diagnostic and therapeutic value.

It is therefore subject of the invention a cell comprising one or more nanoparticles, whose essential features are defined in the first of the annexed claims.

Further subjects of the invention are a composition a plurality of cells, whose essential features are defined in the claim 8 here annexed; a process of preparation of such composition as in the claim 10 here annexed; and the above said composition for use as diagnostic and/or therapeutic agent for the diagnosis and/or treatment of solid tumours, as defined in the claim 12 here annexed.

Further important features of the cell, of the composition and of the composition for use as diagnostic and/or therapeutic agent according to the invention are defined in the dependent claims, also annexed here, and illustrated in the following detailed description.

BRIEF DESCRIPTION OF THE FIGURES

The FIG. 1 shows, overlaid in the same graph, five UV-Vis absorption spectra recorded for five different solutions of gold nanoparticles prepared as described in the Example 1;

the FIG. 2 shows, overlaid in the same graph, two UV-Vis absorption spectra recorded for a solution of gold nanoparticles just prepared as described in the Example 1, and for the same solution after 3 weeks from the preparation;

Figure 3:
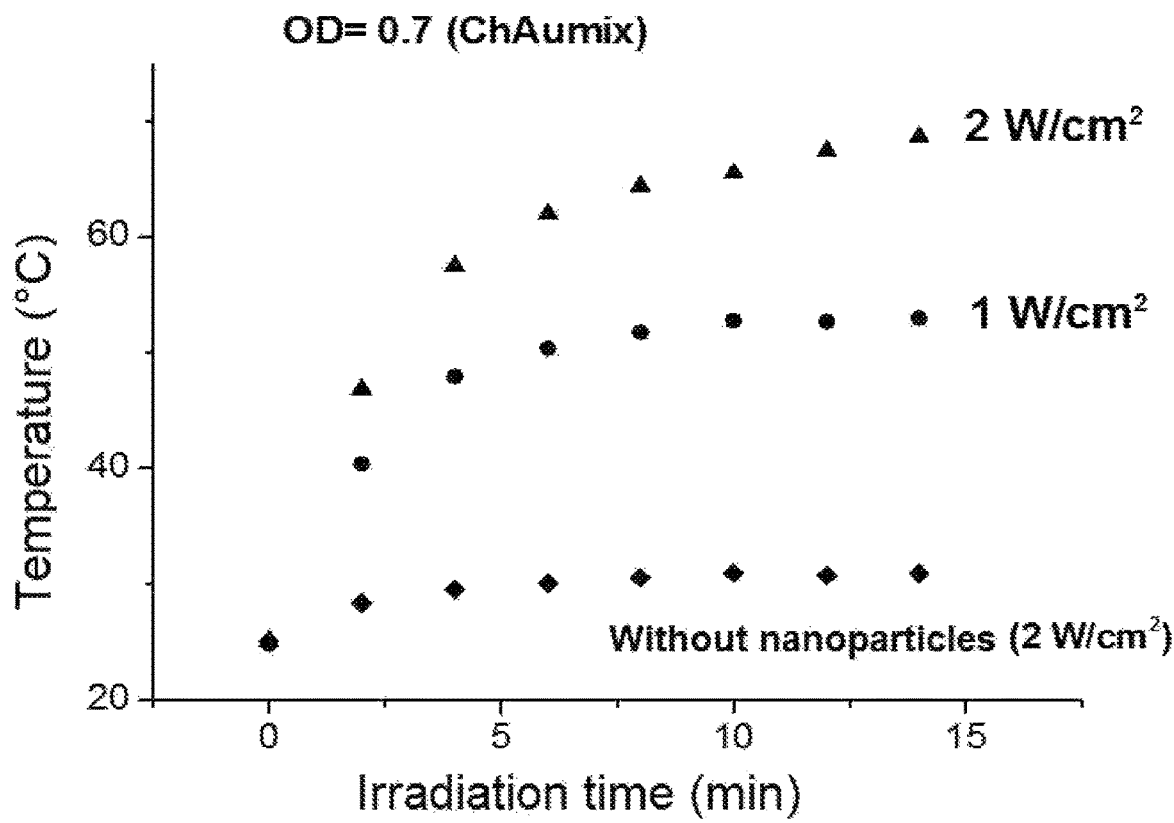
Figure 4:
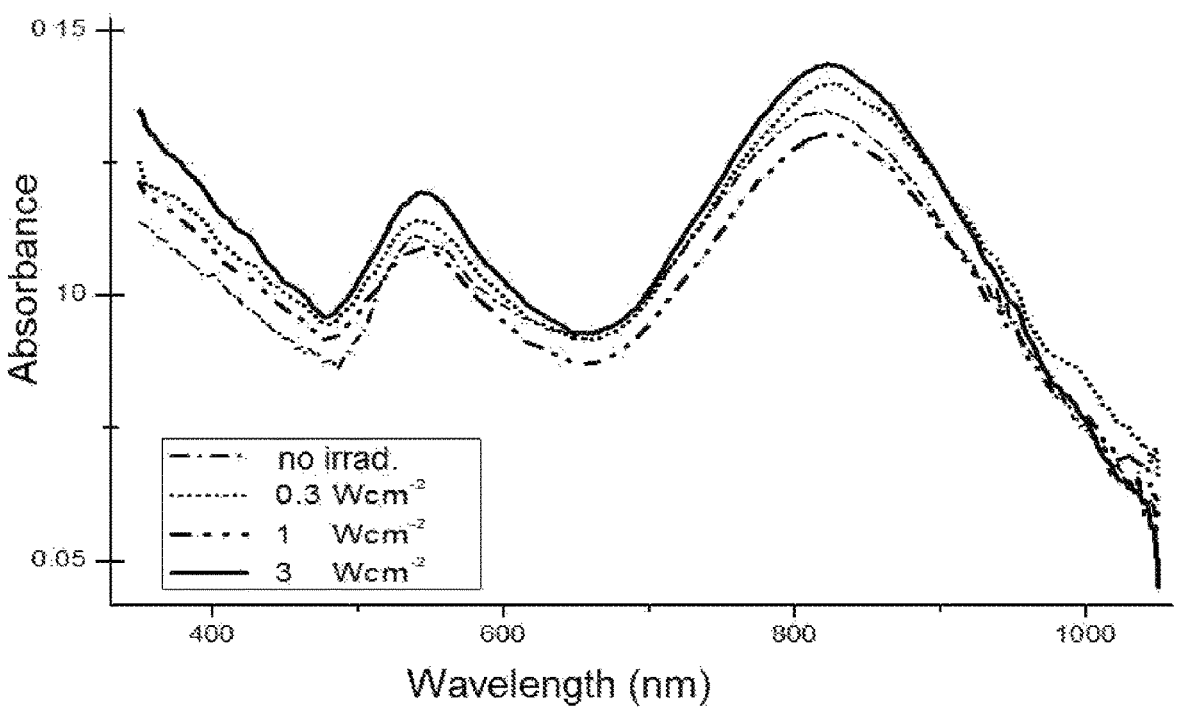
Figure 5:
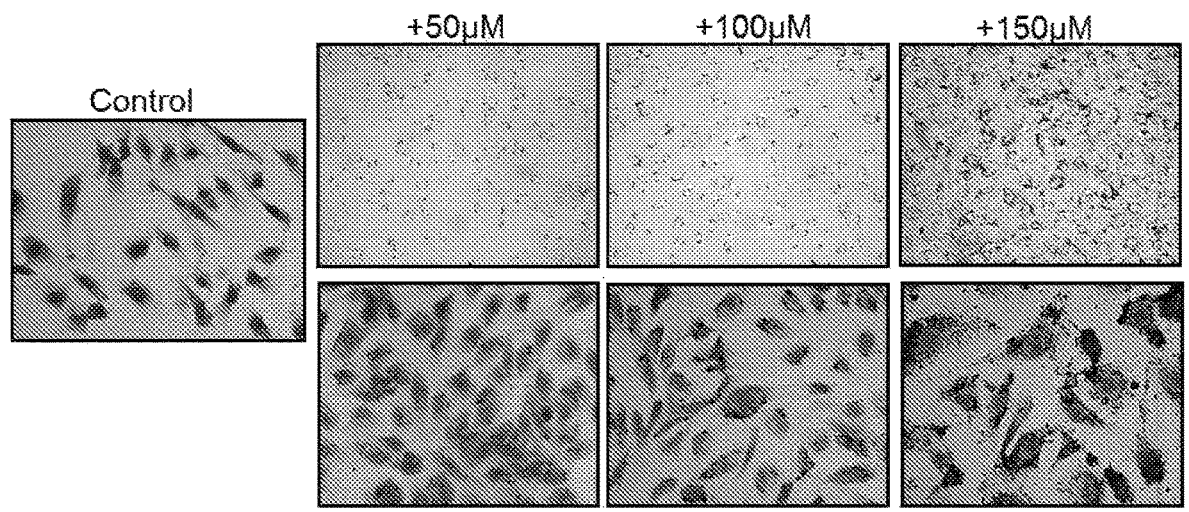
Figure 6:
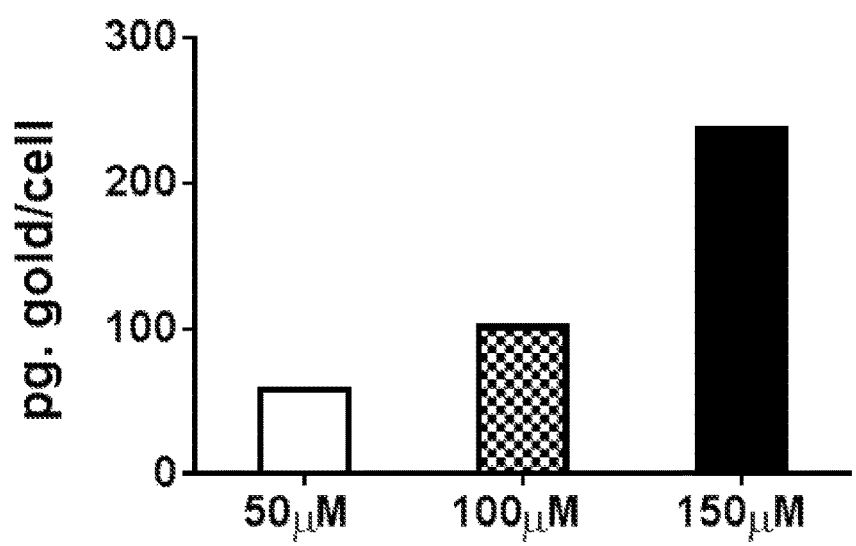
Figure 7:
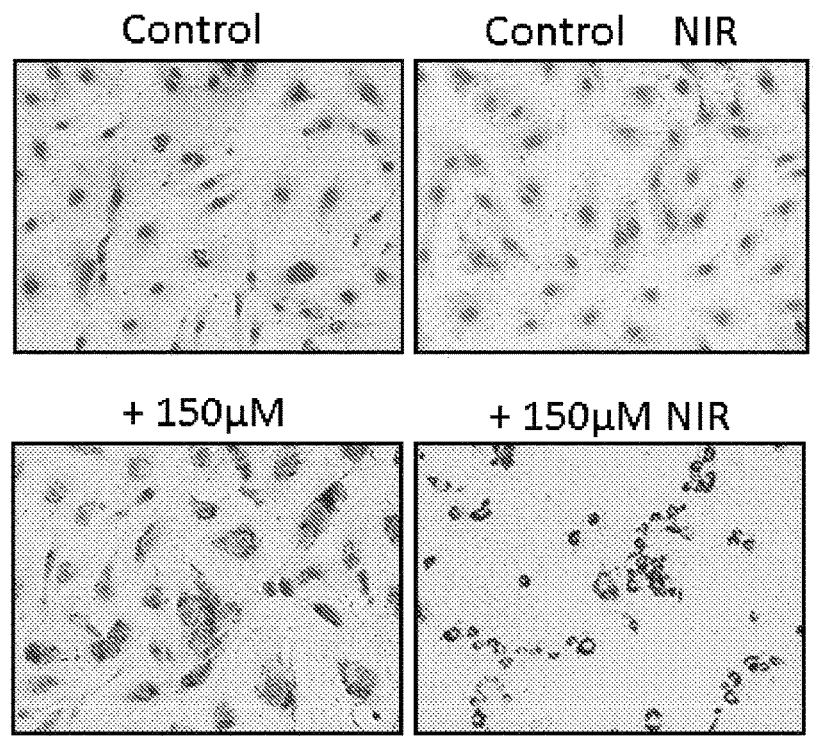
Figure 8:
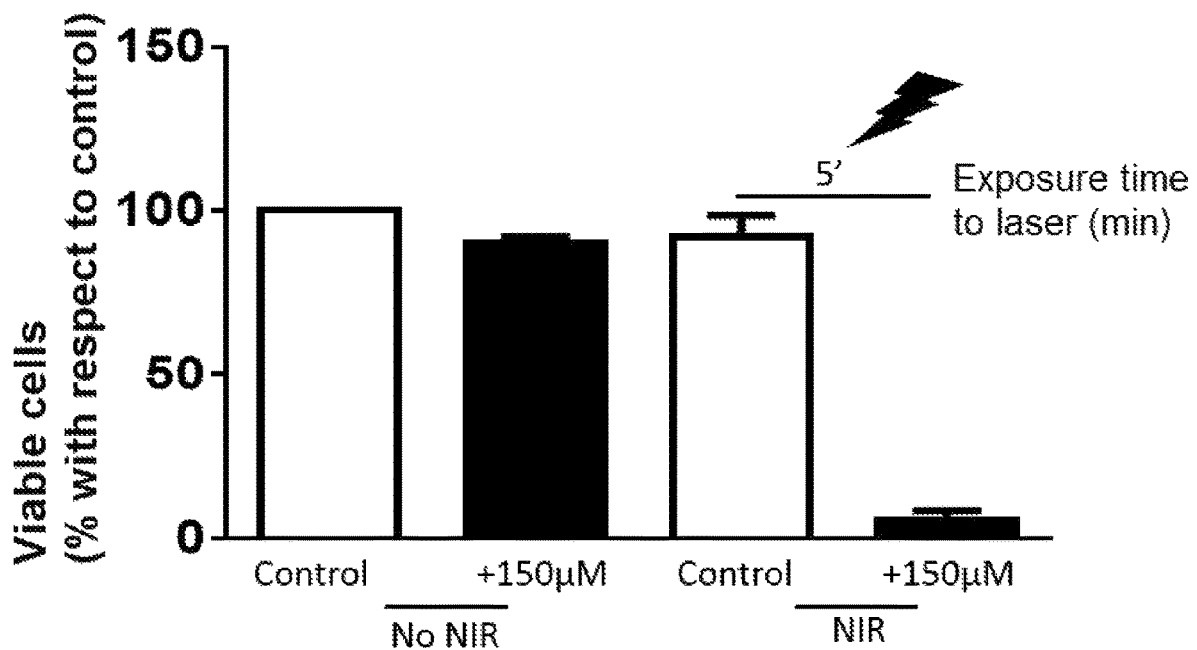
Figure 9:
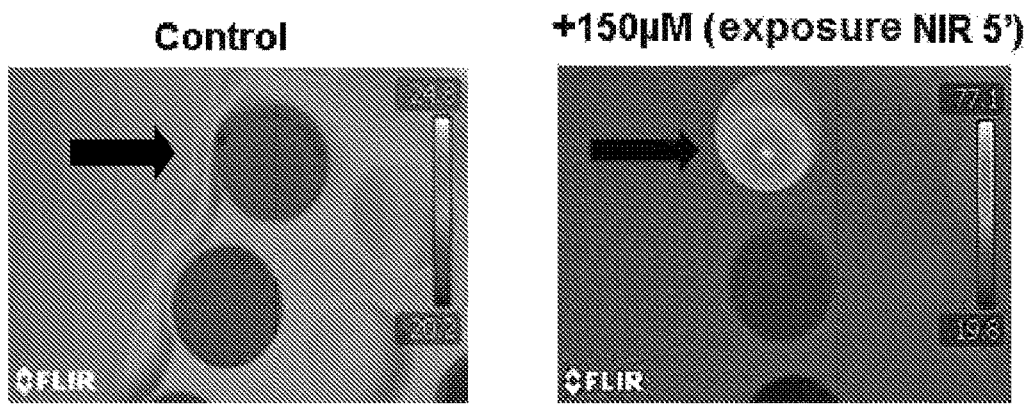
Figure 10:
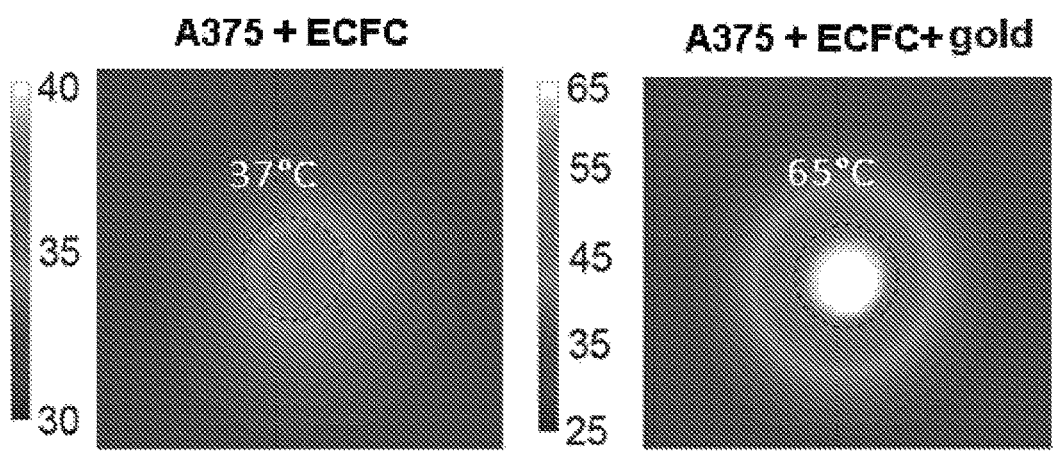
Figure 11:
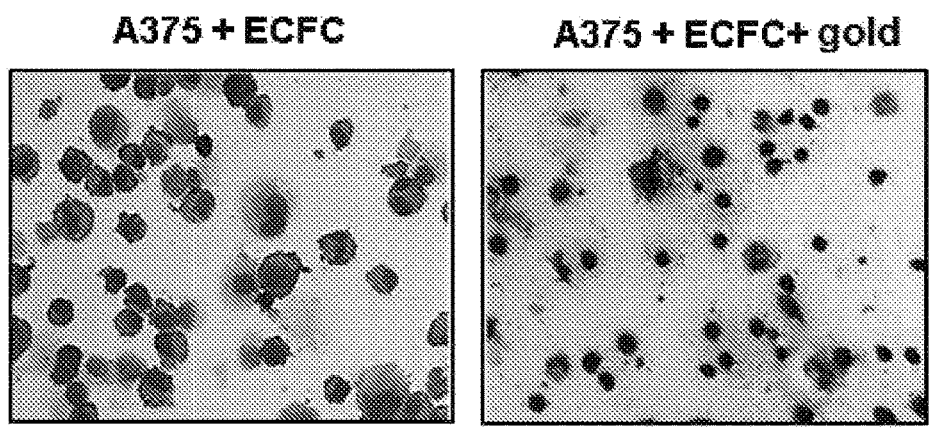
Figure 12:
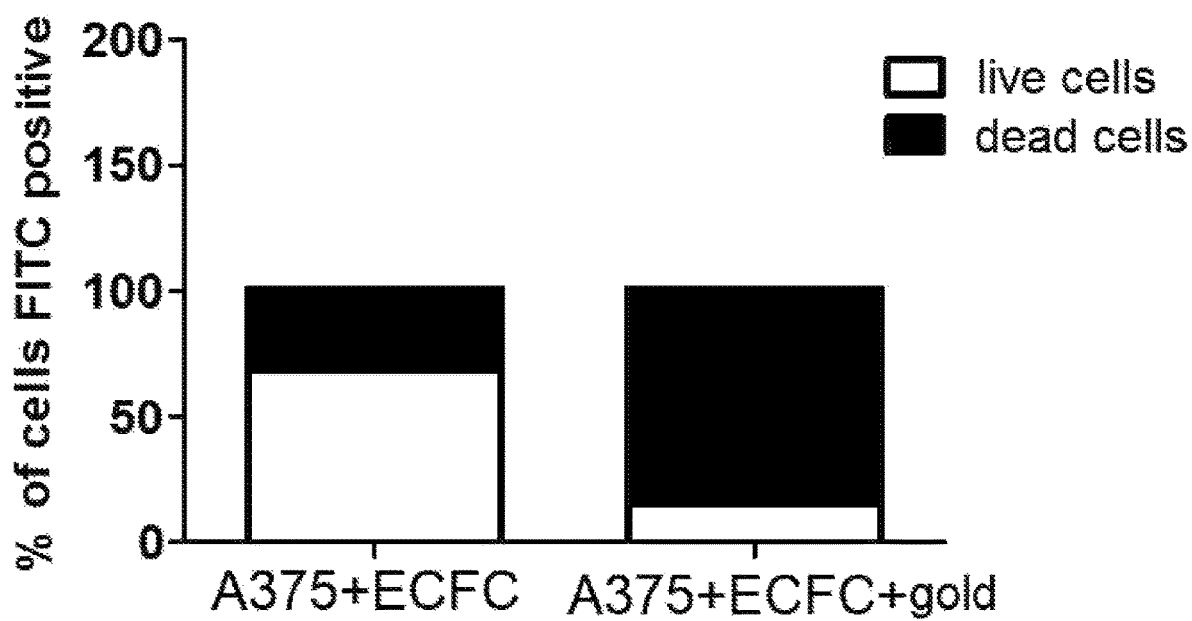

the FIG. 3 shows the increase of temperature following irradiation under different conditions of the same colloidal solution as described in the following Example 2;

the FIG. 4 shows, overlaid in the same graph, the UV-Vis absorption spectra of the colloidal solution after irradiation under different conditions and, as a comparison, of the same solution non-irradiated, as described in the Example 2;

the FIG. 5 shows images acquired with optical microscope for different samples of ECFC cells loaded with gold nanoparticles at different concentrations, obtained as described in the following Example 4;

the FIG. 6 shows, in form of histogram, the amounts of gold incorporated in ECFC cells loaded with the gold nanoparticles as in Example 4, at three different concentrations;

the FIG. 7 shows the optical microscope images of samples of ECFC cells loaded and not loaded with gold nanoparticles, before and after the irradiation with laser irradiation having a peak of emission in the near infrared (NIR), under the conditions described in the following Example 5;

the FIG. 8 shows, in form of histogram, the percentage of viable cells with respect to the control before and after irradiation, always with reference to the experiments described in the following Example 5;

the FIG. 9 shows the images recorded by an infrared camera FLIR after irradiation on a control of ECFC naked cells and on the same cells loaded with gold nanoparticles, as described in the Example 5;

the FIG. 10 shows the profiles of the surface temperatures reached for a mixed cellular culture with ECFC cells loaded and non-loaded with gold nanoparticles according to the invention and melanoma cells after irradiation under the conditions described in the following Example 6;

the FIG. 11 shows the optical microscope images recorded in the cell viability assay using May-Grunwald staining of Example 6;

the FIG. 12 shows, in form of histogram, the percentages of vital and dead cells for the sample of the invention and for the control with ECFC cells non-loaded with the nanoparticles, according to the data obtained from the cell viability assay described always in the following Example 6.

DETAILED DESCRIPTION OF THE INVENTION

The subpopulation of endothelial colony-forming cells (in the following ECFC) is known to be characterised by a high proliferative potential and they may reach over 100 in vitro replications with formation of secondary and tertiary colonies after passages in vitro, they are also characterised by the ability to form in vitro blood vessels (angiogenesis) and by the ability to localise selectively in solid tumours, such as melanoma. As far as the Applicants are aware of, however, it was never disclosed until today the use of these cells as carriers for nanoparticles, whereas on the contrary it was described in the literature the use of stem cells, in particular of mesenchymal stem cells, to convey nanoparticles to target organs in the human body.

The inventors have now unexpectedly found that the ECFC cells loaded with nanoparticles having a gold core stabilised with a coating agent, having an absorption peak in the near infrared and diameter smaller than 100 nm, are an optimal carrier for these latter and for their localization in the tumour mass of solid tumours, such as melanoma. On the contrary, stem mesenchymal cells loaded with the same nanoparticles with a coated, gold core have proved to be much less efficacious in terms of captation of the nanoparticles, so that these stem cells could not in fact be used for the diagnostic and/or therapeutic scopes subject of the present invention.

Not only, inventors have also unexpectedly found that the ECFC cells loaded with the nanoparticles of the invention have a greater ability of being taken by the tumour mass with respect to the same ECFC cells without nanoparticles. Without wanting to be bound to a theory, inventors have collected experimental evidences that link this behaviour to the ability of the nanoparticles, once incorporated in the ECFC cells, of increasing the expression, on the surface of the cell itself, of a certain receptor having a key role in the cells uptake in the tumour mass. More in particular, by means of Western Blotting, it was shown by the inventors an increase in the expression of the CXCR4 receptor on the surface of the ECFC cells when they are loaded with the gold nanoparticles of the invention with respect to the same cells "naked", not loaded with nanoparticles. Furthermore, evidences with experiments in the Boyden chamber have proved how loading the present gold nanoparticles increases of approx. 250% the number of ECFC cells uptaken toward a gradient of SDF1, ligand of the receptor CXCR4 typically produced in the tumour masses. It was finally observed how such increase in the number of cells is blocked by the use of antibodies able to inhibit the interaction between the receptor CXCR4 on the cells surface and the ligand SDF1 produced in the tumour masses.

The nanoparticles of the cells of the invention typically have dimensions smaller than 100 nm, preferably comprised between 4 and 50 nm, are substantially consisting of gold and coated by a stabilizing agent, selected for instance among chitosan and derivatives thereof, such as for instance the carboxymethylchitosan, polyvinylpyrrolidone (PVP), polyethylene glycols and derivatives thereof, such as for example thiolated polyethylene glycols mono- or bi-functional (PEG-SH) or polyethylene glycol orthopyridyldisulphide (PEG-OPSS). Chitosan is the preferred coating agent for use in the nanoparticles of the invention. It is an organic macromolecule, highly biocompatible and of low cost, available in forma of many derivatives on the market, with a great ability to render stable the colloidal solutions of the nanoparticles.

The nanoparticles to be loaded in the cells of the invention can be prepared by a known procedure, very simple and rapid, besides being reproducible, consisting in the reduction of a gold salt, for example tetrachloroauric acid ($HAuCl_4$), by a treatment with sodium thiosulphate ($Na_2S_2O_3$) in aqueous solution, followed by the addition of a stabilizing solution of chitosan. A colloidal solution is thus obtained, perfectly stable for until 15 weeks, even without addition of any surfactants. The concentration of gold in the final colloidal solutions can be easily controlled by varying the starting amounts of reagents, and it is typically equal to approximately 1.4 mM, thus arriving anyway up to approximately 3 mM. The molar ratio between gold and sodium thiosulphate can be moreover varied so as to adjust the infrared extinction band and, according to the present invention, such molar ratio may be comprised between approximately 1.8 (for example 3 mM of gold/1.7 mM of sodium thiosulphate) and approximately 3 (for example 3 mM of gold/1 mM of sodium thiosulphate).

The thus produced colloidal solutions consist in general of a mixture of two populations of nanoparticles, one of aspheric type and one of spheroidal type. While the aspheric nanoparticles substantially contribute to the formation of an extinction spectral band in the near infrared, with a peak around 810 nm, the spheroidal nanoparticles, as long as their dimensions are in the order of 5 nm, can contribute to a band with a peak around 520 nm. Some Authors have reported that spheroidal nanoparticles having dimensions greater than 5 nm, might be consisting of a gold core and a surface shell of gold sulphide (they are after this called "Gold-Gold sulfide nanoparticles", or "GGS-NPs"), therefore in this case they also exhibit a strong absorption in the near infrared. Despite the presence of a not negligible mass of spheroidal nanoparticles not active in the near infrared, the colloidal solutions of nanoparticles of the present invention allow anyway providing a material with an excellent thermotransductive power, as shown in the following experimental examples. In any way, in order to maximise the thermal damage induced by the absorption of the laser radiation by the nanoparticles loaded in the ECFC cells and localised in the tumour mass in vivo, the mixture of nanoparticles obtained by the process described above may also be treated by filtering out the population of spheroidal nanoparticles, so as to obtain a colloidal solution enriched of nanoparticles having specific properties of absorption in the near infrared.

According to a particular embodiment of the present invention the ECFC cells are loaded with nanoparticles as herein defined, further a functionalisation for example with thiolated molecules, i.e. having terminal groups —SH, in particular with polyethylene glycol thiolated (PEG-SH), which has a stabilising and screen function toward the response of the immune system once the loaded cells are introduced into a human body, but it may also have an active function, for instance specific biological actions such as the tumour tagging, whose purpose is the selective marking of the tumour cells. Typically, in order to achieve the marking, the nanoparticles are bioconjugated with specific ligands for overexpressed receptors by the neoplastic cells, as anti-HER2, anti-UPAR or anti-EGFR antibodies. Another specific biological function is the l'optical tracing, wherein the nanoparticles are conjugated with Raman-active reporter molecules, excitable in the near infrared, whose presence can be detected in vivo with minimal interference from the self-fluorescence of the tissues.

The ECFC cells according to the invention comprise for instance from about 50 to about 300 pg of gold per cell, quantified by inductively coupled plasma atomic emission spectroscopy (ICP-AES). The ECFC cells loaded with gold nanoparticles can further comprise at least a marking agent, selected for example between indio[111], and tecnezio[99] (see for example Rodriguez M. et al. "Labelling of platelets with indium-111 oxine and technetium-99 hexamethylpropylene amine oxime: Suggested methods" Eur. J. Nucl. Med. 1999; 26:1614-1616), preferably indio[111].

The present ECFC cells loaded with nanoparticles and marked with the above said marking agents, and in particular with In[111], allow being detected once accumulated in the tumour masses by Single Positron Emission Computed Tomography (SPECT). They represent therefore a powerful diagnostic mean for the localisation of the primary tumour and of possible metastases thereof, besides a targeted therapy of the tumour masses by thermoablation treatment, allowing at the same time following the evolution of the disease and the progressive effect of the treatment.

The ECFC cells loaded with the nanoparticles according to the invention can be obtained by incubating, for a time comprised for example between about 24 and about 48 hours, colloidal solutions of nanoparticles as described herein, with a concentration preferably comprised between 50 and 150 µM, with monolayers of ECFC cells isolated by procedures known to anyone having ordinary skills in the art. The obtained cellular material, subjected to washings in order to eliminate the not endocytosed nanoparticles, comprises ECFC cells loaded with nanoparticles in a percentage higher than 90%, and preferably comprises at least about 96% of the cells loaded with nanoparticles.

The ECFC cells of the present invention can be advantageously obtained also directly from the blood of the patient with tumour, after a stimulation of the hematopoietic marrow with suitable cytokines able to induce the release of endothelial cells in the blood circulation. In this way a customised or "targeted therapy" may be achieved, based on the use of cellular components for each single patient. Differently from the traditional antiblastic chemotherapies, generically attacking all the cells under active proliferation, this therapeutic approach allows attacking selectively and specifically the tumour cells, thus reducing the toxicity and increasing the efficacy of the therapy.

By procedures known to any person with ordinary skills in the art, the composition of the cells so obtained can be further modified, for instance at the aim of including a further diagnostic and/or therapeutic agent and/or a contrast agent. Also without these additional agents, the compositions of the cells loaded with nanoparticles according to the invention are useful for the diagnosis of solid tumours, in particular of melanoma and of its possible metastases, as well as for the treatment of the same tumours by stimulation with a pulsed laser beam, of the nanoparticles localised in the tumour mass.

The compositions of the present invention allow making a diagnosis of localisation and subsequent thermoablation of primary and metastatic melanomas by stimulation of the nanoparticles loaded in the ECFC cells, marked with a suitable marking agent, injected into the blood circulation of the patient suffering from a primary and/or metastatic melanoma. The present compositions have such utility not limited to melanoma, but also extending to a wide range of human tumours, that are in general solid tumours, for which the ability was proved to release the ligand SDF1.

The following examples are provided as a non-limiting illustration of the present invention.

EXAMPLES

Example 1—Synthesis of the Gold Nanoparticles

At room temperature (25° C.) 0.5 ml of an aqueous solution of $Na_2S_2O_3$ have been added quickly to 2.5 ml of an aqueous solution of $HAuCl_4$ in a molar ratio gold/thiosulfate of 2.6. The solution was maintained for 20 seconds in a vortex stirrer and then left to settle for about 10 minutes, during which a change of colour was observed, from yellow to brown to dark red. Completion of the reaction was verified by recording the UV-Vis spectrum of the solution after 30 minutes, then at a further distance of 10 minutes. The solution thus obtained was then added with 0.09 ml of a 0.1% (w/v) solution of high molecular weight chitosan (~$10^6$ Da; degree of deacetylation 79%) in acetic acid at 1% (v/v). The final gold concentration was 1.4 mM. The colloidal solution thus obtained was then left under slow stirring for 6-12 hours before being autoclaved.

The preparation described above was repeated by changing the molar ratio gold/thiosulfate, and in particular by using a ratio gold/thiosulfate of 1.8; 2; 2.4; 2.6; 2.8; 3.

Figure 1:
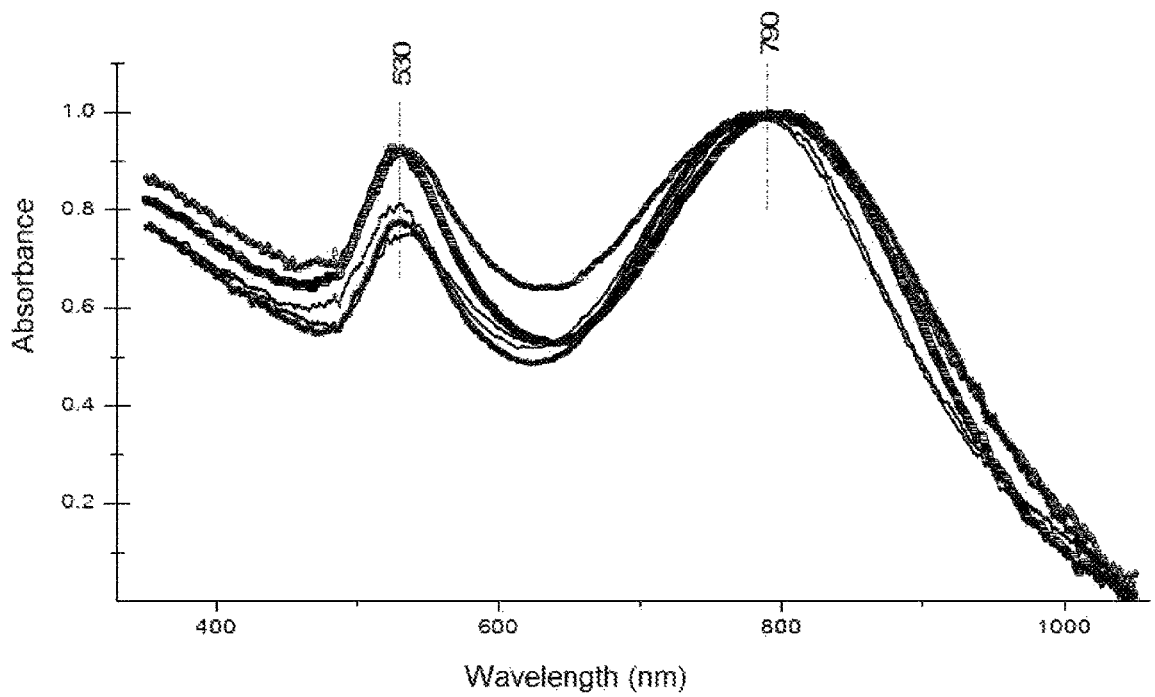

The process of synthesis described above was found completely reproducible from the following experimental test. As a significant indicator of the reproducibility of the synthesis process, the resemblance of the UV-Vis absorbance spectra of the solutions was chosen. By recording the UV-Vis UV spectra of 5 solutions prepared under the same environmental conditions by repeating 5 times the same synthetic method described above with a molar ratio of gold/thiosulphate equal to 2.6, it was possible to verify that the absorbance spectra of the five products are basically superimposable, a sign of the reproducibility of the process used. FIG. 1 illustrates the absorption spectra obtained for the five solutions.

Example 2—Characterisation of the Solutions of Gold Nanoparticles and Chitosan The colloidal solutions obtained as described above in the Example 1 have been studied to evaluate the stability over time, the thermotransductive power, and the photothermal stability under continuous irradiation.

Figure 2:
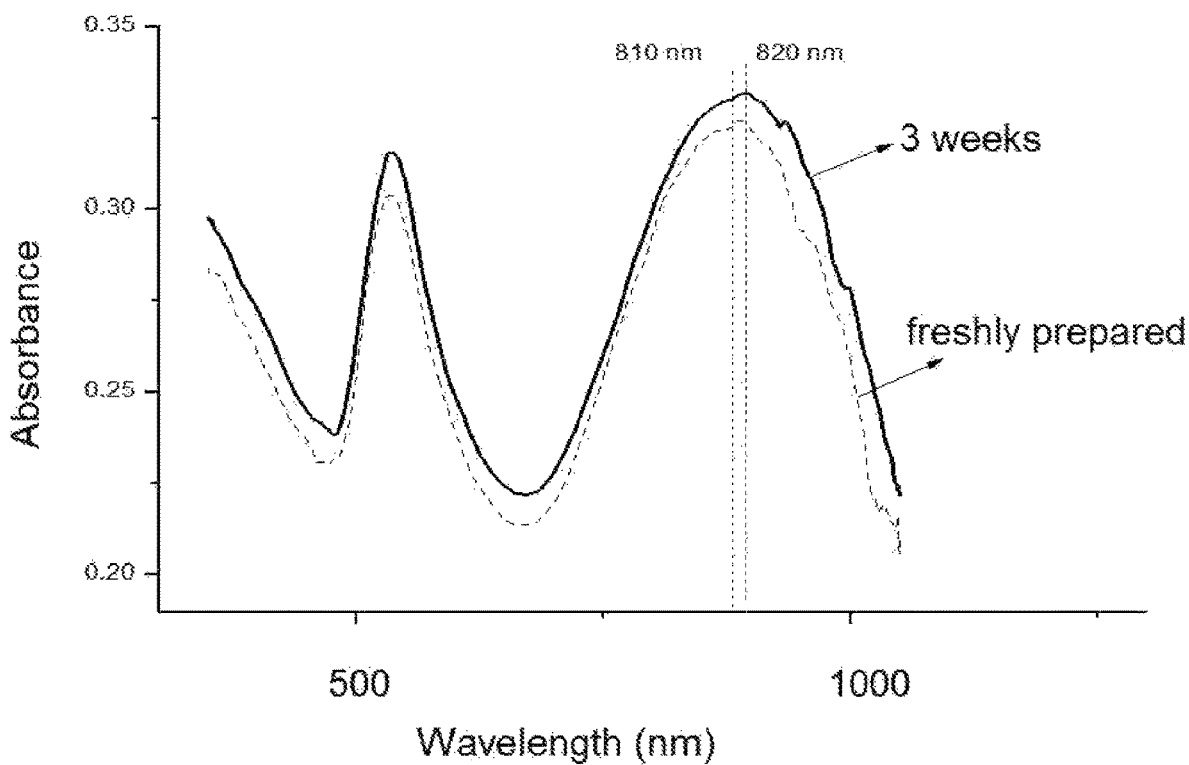

Still on the basis of the UV-Vis absorbance spectra, recorded on the same solution, freshly prepared and after a 3-weeks maturation time, it was possible to verify the stability over time of the prepared solutions as described above, thus obtaining basically superimposable spectra, shown in FIG. 2. Similar results were obtained by prolonging the maturing times of the colloidal solutions up to 15 weeks after preparation.

It was moreover verified the thermotransductive power of the gold nanoparticles solutions of the Example 1 by irradiation of the solutions with a laser of wave length 808 nm and at two different levels of intensity of the laser irradiation, i.e. 1 W/cm$^2$ and 2 W/cm$^2$, and by measuring the increase of temperature in the irradiated solution. In FIG. 3 the variation of temperature can be observed over time for the colloidal solution of the gold nanoparticles with molar ratio gold/thiosulphate of 2.6, at the two different intensities of irradiation and, by comparison, for a solution not containing nanoparticles, irradiated with intensity of 2 W/cm$^2$. Data have been recorded for solutions of thickness equal to 10 mm. As it can be observed from the graph in FIG. 3, after some minutes of irradiation values of hyperthermia are reached (temperature>45° C.) only for the solutions containing the nanoparticles, and also at low levels of intensity of irradiation (1 W/cm$^2$).

On the same colloidal solution having optical density OD=0.7 tests of photothermal stability have been carried out too by continuously irradiating the colloid in a cuvette (thickness of the solution: 2 mm) with a laser diode emitting at the wave length of 808 nm and at three different values of intensity, i.e. 0.3, 1 and 3 W/cm$^2$. FIG. 4 shows the UV-Vis absorbance spectra recorded for the solution irradiated under the conditions said above and, by comparison, for the same solution not irradiated. In FIG. 4 a substantial maintenance of the shape of the spectrum may be observed to indicate the high photothermal stability of the present colloidal solutions following irradiation.

Example 3—Isolation of ECFC Cells and of Mesenchymal Stem Cells (MSC)

Umbilical cord blood units (hereinafter referred to as UBC) have been used with a total number of nucleated cells<1.3×10$^9$ (threshold of suitability for the inclusion of the cords in the hospital bank, established by the Careggi Umbilical Cords Bank in Florence, Italy) after written, free and informed consent of mothers and in accordance with Italian legislation. The ECFC cells were isolated from UBC according to the procedure described in Margheri F. et al. Blood. 2011; 118: 3743-55. The cells were characterized for the expression of selective markers: CD34, CD133, absence of CD45 and appearance of specific endothelial markers (KDR, CD144, CD141, CD105, VWF, CD31) that were monitored by flow cytometry.

The MSCs used as a comparison in the following examples were obtained from the aspirate of hematopoietic bone marrow (hereinafter BM) of patients who provided their written consent, free and informed. The total fraction of nucleated cells (TNCs) from BM samples was obtained by automated procedure with a SEPAX S-100 instrument (Biosafe, Eysins, Switzerland). At the passage (indicated by P) P0 and P6, a cell rate was used for the test of differentiation capacity into adipose and bone tissues, and simultaneously subjected to cytofluorimetric analysis to evaluate the expression of surface antigens such as CD105, CD90, CD73, CD29 and CD44. The MSCs can be expanded in vitro without apparent loss of phenotype and function loss by using an appropriate culture medium, DMEM Low Glucose, added with 20% animal serum and sodium pyruvate.

Example 4—Loading of Cells with Gold Nanoparticles

The ECFC cells isolated as described above in the Example 3 have been loaded with gold nanoparticles by incubation of monolayers of confluent cells with colloidal solutions of gold nanoparticles stabilised with chitosan and, by comparison with gold nanoparticles before the addition of chitosan, prepared as described above in the Example 1, at different concentrations for 24 hours or for 48 hours. The same experiment was repeated also on MSCs isolated by using the same experimental protocol adopted for the ECFCs and described above in the Example 3. After the incubation all the cells were washed with fresh culture medium, detached and characterised for their biological and functional properties, as described below.

The actual incorporation of the nanoparticles in the cells was first of all verified by TEM analysis with an electronic transmission microscope, which highlighted how the presence of chitosan causes a high increase in the uptake into the cells of the nanoparticles, and how already for solutions of nanoparticles having a concentration of 50 µM there is a significant incorporation of the gold nanoparticles.

FIG. 5 illustrates the images acquired by optical microscope with the May-Grunwald stain on ECFC cells and colloidal solutions of the gold nanoparticles with chitosan at concentrations of 50, 100 and 150 µM by using as control the cells treated with water, i.e. the carrier wherein the nanoparticles have been re-suspended at the end of the synthesis. These images highlight how the ECFC cells incorporate the nanoparticles with a dose-dependent kinetics. The amount of gold actually incorporated after 24 hours of incubation was then quantified by inductively coupled plasma mass spectrometry (ICP-MS); in FIG. 6 the thus obtained values are indicated in the form of histogram, and show a dose-dependent enrichment of the ECFC cells, wherein 60, 100 and 250 pg of gold per cell are incorporated starting from solutions of nanoparticles containing gold concentrations respectively equal to 50, 100 and 150 µM.

At equal concentration of nanoparticle solutions and incubation conditions, the isolated MSC cells as described above in Example 3 revealed a lower uptake of the nanoparticles (equal to approximately 70%) compared to the ECFC cells, showing the unexpected goodness of the latter even with respect to stem cells.

Example 5—Evaluation of the Cells Loaded with Gold Nanoparticles

The cells loaded with gold nanoparticles obtained as described above in Example 4 starting from solutions of various concentrations were subjected to a metabolic assay based on the activity of 3-(4,5-dimethylthiazol-2-yl)-2,5-diphenyltetrazonium bromide (or MTT), which measures the mitochondrial enzymatic activity, and to a Trypan blue assay, thus finding that cell viability was basically maintained even after incorporation of the nanoparticles. These assays have been repeated, with the same result of cellular viability maintained, also on cells with embedded nanoparticles, also subjected to irradiation with light in the near infrared (wavelengths in the range 700-1100 nm, corresponding to the so-called window of tissue transparency).

It has also been verified that the capillary in vitro morphogenesis of ECFCs is not modified as a result of the nanoparticles uptake, as well as their invasive capacity remains unchanged.

Finally, the thermotransductive response of the ECFC cells loaded with gold nanoparticles was evaluated by in vitro irradiation with a laser source having a peak of emission at wavelength of 808 nm, and by a real-time measurement of the increase of temperature thus generated by IR thermography with a FLIR thermocamera. This study was performed with ECFC cells incubated for 24 hours with a solution of nanoparticles having a gold concentration of 150 µM, by using ECFCs without nanoparticles as a control. In this experiment, power densities, mediated on a 4 mm diameter illumination spot (corresponding to an encircled energy=97%), varied from 3 W/cm$^2$ up to 5 W/cm$^2$, while the exposure time was fixed at 5 minutes. For the cells loaded with nanoparticles temperatures were observed beyond the limits of the physiological threshold, ranging from 50.6° C. up to 62° C. that were sufficient to induce the cell death. The irradiation with light in the near infrared did not alter the viability of the control cells, not containing nanoparticles, as was the result of the morphological analysis with the May-Grunwald stain (FIG. 7), as well as with Trypan blue (FIG. 8), and the irradiation did not increase their temperature (FIG. 9).

Example 6—Evaluation of the Thermoablative Efficiency of ECFC Cells Loaded with Nanoparticles on Mixed Cultures with Melanoma Cells In order to evaluate the "anti-tumour" therapeutic potential of the ECFCs loaded with gold nanoparticles, a cellular suspension consisting of cells of human melanoma stabilised in vitro A375 and of ECFCs loaded with nanoparticles were irradiated with light in the near infrared. In order to evaluate the cellular death of the tumour cells of the suspension, before irradiation the A375 cells were marked with carboxyfluoresceine succinimidyl ester (in the following CFSE, Carboxyfluorescein Succinimidyl ester), a lipophilic fluorescent molecule, able to diffuse freely through the cellular membranes. Once incorporated by the vital cells, the CFSE is no more able to cross the membrane and remains in the cytoplasm of the cell for several weeks, without being of damage for the cellular functionality. A mixed cellular solution was prepared composed by $1 \times 10^6$ of A375 cells marked with CFSE and $5 \times 10^4$ of ECFC cells loaded and not loaded with nanoparticles. 150 µl of the cellular solution described above was placed in a suitable well and then exposed to irradiation with an infrared laser beam Several tests have been carried out with different densities of power and a different time of exposure and, for each experimental variation, the increase of temperature due to the absorption of the nanoparticles was traced and recorded in real time with a thermocamera FLIR, as described above. In FIG. 10 the profiles are reported for the surface temperatures reached by the mixed cellular culture in the experimental conditions. The cellular death of the melanoma cells present in the irradiated mixed culture was then evaluated by morphological analysis (May-Grunwald stain) (FIG. 11) and by cytofluorimetric analysis by measuring the fluorescence that can be only referred to the presence of viable cells. In the presence of ECFC cells loaded with nanoparticles an almost complete loss of fluorescence was observed and this indicates that approximately 93% of the tumour cells were killed. On the contrary, following to the irradiation of co-cultures containing ECFC cells not loaded with nanoparticles the viability of the A375 cells exceeds 75%. The data obtained are illustrated in form of histogram in the FIG. 12.

Example 7—Marking of the Cells Loaded with Nanoparticles

The ECFC cells loaded with nanoparticles have been marked following the procedure described in Gholamrezanezhad A., et al. "In vivo tracking of 111In-oxine labeled mesenchymal stem cells following infusion in patients with advanced cirrhosis" Nucl Med. Biol 2011; 38: 961-967. In brief, the ECFC cells have been re-suspended in a culture medium containing 100 μCi of $^{111}$In 8-oxyquinoline/$10^6$ cells for 30 minutes at room temperature; they were then washed and centrifuged before being used in the experiments described below by injections in animals.

Example 8—Design of the Animal Model of Metastatic Melanomas

All the following procedures involving animals have been carried out in accordance with the national guidelines, approved by the ethical committee of the Animal Welfare Office of Italian Ministry of Labour and in accordance with legal mandates and Italian guidelines for the care and maintenance of laboratory animals. The following lines of human melanoma stabilised in vitro have been used, purchased by the American Type Culture Collection (ATCC): A375 (from a skin biopsy of a malignant human melanoma) and A375-M6, derived from the parent line A375 by culturing cells experimentally obtained from metastatic pulmonary nodules. The cells have been cultured in Dulbecco's modified Eagle's medium (DMEM 4500, Gibco) supplemented with the 10% of foetal calf serum (FCS), at 37° C. in a humidified atmosphere containing 5% of $CO_2$. The in vivo experiments have been carried out in mice SCID bg/bg (severe combined immuno-deficiency, with additional mutation in the expression of the Natural Killer Lymphocytes bg/bg), of 6 to 8 weeks old and the solid tumours were obtained by subcutaneous injection of 1.5 or $2 \times 10^6$ of viable A375 or of A375 M6, alone or co-injected together with the MSCs obtained as described above in the Example 3. The tumour development was monitored at regular intervals by measuring the diameter of the tumours (groups of 10 mice for each experimental point, in total 60 animals for each experiment). The mice with tumours were sacrificed 25 days after the implant, the tumours were removed and treated for the histological analysis. The intra-tumour angiogenesis was determined on the basis of the microvascular density by immunohistochemical staining with anti-CD31 antibody, and expressed as number of vessels/microscopic field.

In mice according to this model of metastatic tumours, when their tumour had reached a diameter of 0.5 cm, approximately $1 \times 10^6$ of cells loaded with nanoparticles and marked with $^{111}$In, obtained as described above in the Example 7, were injected in the caudal vein of the animals. The marking with $^{111}$In has allowed following the localisation of the injected cells by positron emission tomography (PET). It was thus observed that, after 18 hours from injection, the cells marked and loaded with nanoparticles were localised in the melanoma, where they were still present 25 days after the injection. On the basis of the localisation indicated by the PET, the melanoma was subjected to stimulation with a pulsed laser beam until the complete cauterization of the tumour mass. The same procedure was used for the thermoablation of the metastases, reached both by a laser needle electrode and by optical fibres. On these animals it was moreover observed, always by PET, that the cells marked and loaded with nanoparticles, concentrated in the kidneys, disappeared within 3 hours after the appearance in the kidneys, proving a relatively rapid excretion from the kidneys.

The invention claimed is:

1. A cell comprising:
said cell loaded with a mixture of nanoparticles exhibiting a peak of absorbance at about 810 nm measured by UV-Vis spectroscopy and nanoparticles exhibiting a peak of absorbance at about 520 nm measured by UV-Vis spectroscopy, wherein said cell is an endothelial colony forming cell and said nanoparticles exhibiting a peak of absorbance at about 810 nm and nanoparticles exhibiting a peak of absorbance at about 520 nm are nanoparticles with a core of gold stabilized by a coating agent,
wherein said nanoparticles exhibiting a peak of absorbance at about 810 nm have a diameter smaller than 100 nm,
wherein said coating agent is chitosan, and
wherein said nanoparticles exhibiting a peak of absorbance at about 810 nm exhibits a thermotransductive effect at about 808 nm with a laser.

2. The cell according to claim 1, wherein said nanoparticles exhibiting a peak of absorbance at about 810 nm have a diameter ranging between 4 and 50 nm.

3. The cell according to claim 1, wherein the cell contains from about 50 to about 300 pg of gold in the form of said nanoparticles.

4. The cell according to claim 1, further comprising a marking agent selected from the group consisting of $^{111}$In and $^{99}$Tc.

5. The cell according to claim 4, wherein said marking agent is $^{111}$In.

6. A composition comprising a plurality of endothelial colony forming cells, wherein at least 90% of said cells is as defined in claim 1.

7. The composition according to claim 6, further comprising a diagnostic agent, a therapeutic agent, or a contrast agent.

8. A process for the preparation of a composition as defined in claim 6, comprising a step of incubation of monolayers of endothelial colony forming cells with aqueous solutions of nanoparticles exhibiting a peak of absorbance at about 810 nm.

9. The process according to claim 8, wherein the concentration of said nanoparticles in said solutions is between 50 and 150 μM.

10. The composition as defined in claim 6, for diagnostic or therapeutic agent in the diagnosis or treatment of a solid tumour and metastases thereof.

11. The composition according to claim 10, wherein said solid tumour is a melanoma.

12. The cell according to claim 1, wherein said cell exhibits increased expression of CXCR4 surface receptor as compared to a cell not loaded with said nanoparticles exhibiting a peak of absorbance at about 810 nm.

13. The cell according to claim 1, when said endothelial colony forming cell exhibits increased internalization of said nanoparticles exhibiting a peak of absorbance at about 810 nm as compared to a mesenchymal stem cell.

* * * * *